United States Patent [19]

Nair et al.

[11] Patent Number: 5,078,994
[45] Date of Patent: Jan. 7, 1992

[54] MICROGEL DRUG DELIVERY SYSTEM

[75] Inventors: Mridula Nair, Penfield; Julia S. Tan, Rochester, both of N.Y.

[73] Assignee: Eastman Kodak Company, Rochester, N.Y.

[21] Appl. No.: 508,767

[22] Filed: Apr. 12, 1990

[51] Int. Cl.$^5$ .............................................. A61K 31/74
[52] U.S. Cl. .................................. 424/501; 424/487; 424/78.31; 523/105; 523/409; 523/412; 523/522; 524/522; 526/320
[58] Field of Search ............... 428/402; 424/486, 78, 424/79, 487; 524/522; 523/105

[56] References Cited

U.S. PATENT DOCUMENTS

| | | | |
|---|---|---|---|
| 4,138,383 | 2/1979 | Rembaum et al. | 260/29.7 |
| 4,329,332 | 5/1982 | Couvreur et al. | 424/497 |
| 4,424,311 | 1/1984 | Nagaoka et al. | 525/303 |
| 4,622,367 | 11/1986 | Horák et al. | 428/402 |
| 4,891,324 | 1/1990 | Pease et al. | 428/402 |

FOREIGN PATENT DOCUMENTS 240424 3/1987 European Pat. Off. .

OTHER PUBLICATIONS

Poste et al., Biotechnology (Dec. 1983), pp. 869–877.
Couvreur et al., *Polymeric Nanoparticles and Microspheres*, CRC Press, Boca Raton, Fla., pp. 27–93.
Andrade et al., Adv. Poly. Sci. 79:1–63 (1986).
Nagaoka et al., *Polymers as Biomaterials* Plenum Press, pp. 361–374 (1984).
*Journal of Pharmaceutical Sciences*, vol. 78, No. 6, Jun. 1989, "Blood Clearance and Organ Distribution of Intravenously Administered Polymethacrylic Nanoparticles in Mice".

Primary Examiner—Thurman K. Page
Assistant Examiner—Robert H. Harrison
Attorney, Agent, or Firm—J. Jeffrey Hawley

[57] ABSTRACT

A copolymer microparticle is presented which is derived from at least about 5 weight percent of free carboxylic acid group-containing vinyl monomers, monomers which have a poly(alkylene oxide) appended thereto, oleophilic monomers and other nonionic hydrophilic monomers. Microgels containing these copolymers having a median water swollen diameter of about 0.01 to about 1.0 micrometer are disclosed. Pharmaceutical and diagnostic compositions are disclosed comprising a therapeutic or diagnostic agent and microgels comprising a copolymer derived from at least about 5 weight percent of non-esterified carboxylic acid group-containing vinyl monomers, oleophilic monomers and other nonionic hydrophilic monomers, with the proviso that when the median water swollen diameter of the microgels is 0.1 micrometer or greater, at least 5 weight percent of the monomers have a poly(alkylene oxide) appended thereto. Diagnostic and therapeutic methods are also disclosed wherein the microgels are substantially protein non-adsorbent and substantially refractory to phagocytosis.

7 Claims, 8 Drawing Sheets

MICROGEL DRUG DELIVERY SYSTEM

BACKGROUND OF THE INVENTION

Polymeric devices that steadily release controlled amounts of therapeutic agents are useful to overcome variations in blood levels of these agents that often occur with administration, either orally or by injection. Such devices, including implants, transdermal and parenteral drug delivery materials, and polymeric microspheres have been found to be extremely useful for this purpose. Rembaum et al, U.S. Pat. No. 4,138,383; Yen et al, U.S. Pat. No. 4,157,323; Poste et al, Biotechnology, (December 1983), pp. 869-877.

The use of microsphere drug delivery systems enables a therapeutic agent to be released in a specified area or over a specified time period. The polymer which constitutes the microsphere particle must be able to form a stable attachment with the therapeutic agent through covalent bonding or physical adsorption or entrapment to avoid premature release in the host organism, but the attachment must also be reversible to enable release of the therapeutic agent at the appropriate site.

The size of the particles is an important parameter which governs the efficacy of the drug delivery system. Microsphere particles which are especially useful are nanoparticles which are small colloidal particles of less than about 1 micrometer in diameter. Couvreur et al, in *Polymeric Nanoparticles and Microspheres*, Guiot, P. and Couvreur, P., ed., CRC Press, Boca Raton, Fla., pp. 27-93.

It is advantageous to incorporate active therapeutic agents, e.g., drugs, into carrier polymer particles, or microspheres, for administration into the blood stream of a host mammal rather than inject the agents themselves. This is to facilitate drug solubilization, avoid rapid degradation, and toxicity, and to control blood levels of the agent. However, after intravenous injection, most types of microspheres tend to be cleared rapidly from the blood by macrophages of the reticuloendothelial system (RES).

This difficulty is due to the adsorption of certain blood proteins onto the surfaces of the microspheres. The presence of these adsorbed proteins results in the uptake of the particles by macrophages and their rapid clearance from blood by the RES. Since the major part of this process occurs within the lever, microspheres can easily be targeted to the Kupffer cells of the liver, and to a lesser extent to spleen and bone marrow. Such "passive targeting is advantageous when the objective is imaging these organs in a diagnostic method or trying to achieve the slow release of carrier-entrapped drugs after uptake into macrophages within these organs. However, it sequestration at other sites is required, when it is necessary to prevent the normal RES clearance.

To deliver drugs, for example, to a tumor outside the RES, it is necessary to avoid RES clearance of the drug and carrier in order to achieve prolonged circulation in the blood. Additionally, it is necessary to be able to pass across the microvasculature to the tissue/organ site in order to have adequate sequestration in the target tissue. RES clearance can be suppressed either with RES-blockading agents, or by controlling the surface characteristics of particles to make them less susceptible to serum protein mediated RES clearance.

If particles, however, acquire a coating of serum factors (serum proteins), accelerated RES-mediated clearance occurs. Protein adsorption on film surfaces can be reduced by the attachment of polyethylene oxide chains to the polymer material. Andrade et al, Adv. Poly. Sci. 79: 1-63 (1986); Nagaoka et a, in *Polymers as Biomaterials* (Shalaby et al, eds.) Plenum Press, pp. 361-374 (1984); U.S. Pat. No. 4,424,311.

Polyethylene oxide (PEO) has been found to be an effective polymer to attach to a film surface for producing low protein adsorption and low cell adhesion characteristics, due to its high mobility, unique solution properties, molecular conformation in aqueous solution and steric stabilization effects. PEO-water interfaces have very low interfacial free energies, and thus low driving forces for adsorption.

SUMMARY OF THE INVENTION

The present invention relates to copolymer microparticles comprising poly(alkylene oxide) containing monomers and to microparticles of a swellable latex copolymer which are useful for the administration of therapeutic and diagnostic agents.

More particularly, the present invention relates to copolymer microparticles that are derived from:
 a) at least about 5 weight percent of free carboxylic acid group-containing monomers;
 b) monomers that have a poly(alkylene oxide) group appended thereto;
 c) oleophilic monomers; and
 d) other nonionic hydrophilic monomers.

The copolymers of the present invention form substantially protein non-adsorbent microparticles.

The present invention also relates to swellable microgel polymer particles having a median water swollen diameter in the range of from about 0.01 to about 1.0 micrometer, preferably in the range of from about 0.02 to about 0.5 micrometer. The polymer particles can be derived from carboxylic acid group containing monomers, oleophilic monomers and nonionic hydrophilic monomers with proviso that when the median water swollen diameter is greater than about 0.1 micrometer, at least about 5 weight percent of the monomers have a poly(alkylene oxide) appended thereto. When some monomers have a poly(alkylene oxide) appended thereto there can be a corresponding decrease in the number of the other nonionic hydrophilic monomer groups of the resulting polymer. The microgel polymer particles are substantially protein non-adsorbent and substantially refractory to phagocytosis and to clearance by the RES when administered to a host mammal.

This invention also relates to pharmaceutical compositions comprising swellable microgel polymer particles of the present invention that have a therapeutic agent associated therewith.

This invention further relates to diagnostic compositions comprising swellable microgel polymer particles of the present invention that have a diagnostic agent associated therewith.

This invention also relates to methods of treatment in which a therapeutically effective amount of a therapeutic agent, which is released over a prescribed time period from particles of the present invention, is administered to a host mammal.

This invention further relates to diagnostic methods in which particles of the present invention associated with a diagnostic agent are administered to a host mammal.

DETAILED DESCRIPTION OF THE INVENTION

The present invention is directed to copolymer microparticles comprising from about 5 to about 30, preferably from about 5 to about 25 weight percent of recurring units derived from free carboxylic acid group-containing monomers; from about 1 to about 25 percent of recurring units derived from vinyl monomers that have a poly(alkylene oxide) group appended thereto; from about 20 to about 90, preferably from about 45 to about 65 weight percent of recurring units derived from oleophilic monomers; and from about 5 to about 40, preferably from about 20 to about 35 weight percent of recurring units derived from other nonionic hydrophilic monomers. The copolymers of the present invention can also contain from about 0 to about 25, preferably from about 0.5 to about 10 weight percent of recurring units derived from cross-linking monomers having two or more addition-polymerizable vinyl groups that produce a swellable three-dimensional polymer network upon polymerization.

The present invention is also directed to swellable microgel polymer particles having a median water swollen diameter in the range of from about 0.01 to about 1.0 micrometer, preferably in the range of from about 0.02 to about 0.5 micrometers. When the polymer particles have a median water swollen diameter of less than 0.1 micrometer, the polymers can comprise from about 5 to about 30, preferably from about 5 to about 25 weight percent of recurring units derived from carboxylic group-containing monomers; from about 20 to about 90, preferably from about 45 to about 65 weight percent of recurring units derived from oleophilic monomers; and from about 0 to about 40, preferably from about 20 to about 35 weight percent of recurring units derived from nonionic hydrophilic monomers. When the particles have a median swollen diameter of 0.1 micrometer or greater from about 5 to about 25 percent of the monomers have a poly(alkylene oxide) group appended thereto. The amount of recurring units derived from poly(alkylene oxide) group-containing monomer units and other nonionic hydrophilic monomers should be at least 10 weight percent of the total weight of the polymer.

The pendant poly(alkylene oxide) groups may be attached to the monomer prior to polymerization or grafted to the polymer.

The particles of the present invention are expected to be able to pass through the microvaculature and minimize adsorption of serum proteins, thus prolonging residence in the circulation and facilitating drug delivery. They can also be utilized in other applications, e.g., in in vivo diagnostic applications, where adsorption to proteins is to be avoided. When the median swollen diameter of the particles is 0.1 micrometer or greater, the presence of a poly(alkylene oxide) group increases resistance to protein adsorption.

The term "carboxylic acid group-containing monomers" as used herein, refers to vinyl monomers containing a free carboxylic group or salts thereof attached thereto.

Exemplary free carboxylic acid group-containing monomers include acrylic acid, methacrylic acid, citraconic acid, alpha-chloroacrylic acid, 3-acryloyloxypropionic acid, itaconic acid, fumaric acid, maleic acid, crotonic acid, and the like.

Exemplary vinyl monomers that have a poly(alkylene oxide) group appended thereto are poly(alkylene oxide) acrylates and methacrylates such as poly(ethylene oxide)acrylate and poly(ethylene oxide)methacrylates and poly(alkylene oxide)acrylamides and methacrylamides such as poly(ethylene oxide)acrylamide and poly(ethylene oxide)methacrylamide, and the like.

The term "poly(alkylene oxide)" as used herein refers to oligomers and polymers derived from alkylene oxides. The poly(alkylene oxide) can range in molecular weight from about 85 to about 5000, preferably from about 100 to about 1000. The oligomers and polymers can form an ester linkage with the carboxy group of carboxy group-containing monomers.

Exemplary poly(alkylene oxides) include poly(ethylene oxide) and poly(propylene oxide), and can include block copolymers of poly(ethylene oxide) and poly(propylene oxide). Poly(ethylene oxide) is the most preferred poly(alkylene oxide).

The term "oleoplilic monomers" as used herein refers to alpha, beta-ethylenically unsaturated hydrocarbon group-containing monomers.

Exemplary oleophilic monomers include acrylic esters, vinyl ether and styrene monomers such as methyl acrylate, methyl methacrylate, ethyl acrylate, n-butyl acrylate, benzyl acrylate, n-hexyl methacrylate, 2-ethylhexyl methacrylate, methyl vinyl ether, styrene, chlorostyrene, vinyltoluene, and the like.

The term "other nonionic hydrophilic monomers" as used herein, refers to monomeric compounds in addition to those monomers described above containing poly(alkylene oxide) groups, containing polar groups such as hydroxy, thiol, amide, and the like.

Exemplary nonionic hydrophilic monomers include acrylic esters, such as 2-hydroxyethyl acrylate, 2-hydroxyethyl methacrylate, 2,3-dihydroxypropyl acrylate, 2,3-dihydroxypropyl methacrylate, 2-hydroxypropyl acrylate, 2-hydroxyethyl acrylamide, 2-hydroxyethyl methacrylamide, 2,3-dihydroxypropyl acrylamide, 2,3-dihydroxypropyl methacrylamide and the like.

The term "cross-linking monomers" as used herein refers to polyfunctional molecules i.e., molecules having two or more addition-polymerizable vinyl groups that are capable of polymerization in the form of a 3-dimensional, i.e., crosslinked, polymer network.

Exemplary cross-linking monomers include ethylene diacrylate, ethylene dimethacrylate, divinylbenzene, N,N'-methylenebisacrylamide, allyl acrylate, propylidyne triacrylate, and the like.

The term "microgel" as used herein refers to uncrosslinked, insoluble, but water swellable, particles and crosslinked insoluble swellable particles. It includes aqueous dispersions of insoluble but swellable polymer particles where the aqueous insolubility results from crosslinking and/or the incorporation of oleophilic monomers.

Copolymers with different compositions of monomers and different polyalkylene oxide chain lengths, are contemplated. In a preferred embodiment, the poly(alkylene oxide), such as polyethylene oxide or polypropylene oxide, can be esterified to the carboxy group of recurring units derived from a carboxy acid group-containing vinyl monomer.

A preferred copolymer of the present invention comprises recurring units derived from methyl methacrylate, poly(ethylene oxide)methacrylate and methacrylic acid monomers.

Another preferred polymer of this invention is poly[methyl methacrylate-co-poly-(ethylene oxide)methacrylate-co-methacrylic acid-co-ethylene dimethacrylate] preferably having a weight ratio of 57/30/10/3 with the poly(ethylene oxide) having a molecular weight of about 100 to 1000.

Preferred embodiments of the present invention are a latex or microgel comprising copolymers of the present invention that have a median water swollen diameter of about 0.01 to about 1.0 micrometers, and particularly about 0.02 to about 0.5 micrometer and are administerable to a host mammal. Such a latex or microgel is substantially protein nonadsorbent and substantially refractory to phagocytosis and to clearance by the RES of the host mammal.

In a particularly preferred embodiment, the copolymers of the present invention have a therapeutic agent associated with them.

The term "associated" as used herein in its various grammatical forms is intended to mean that the therapeutic agent is attached to the copolymers by chemical bonding, physical adhesion or physical immobilization.

The term "therapeutic agent" as used herein includes biologically active substances which are effective in the treatment of a physiologic disorder, pharmaceuticals, enzymes, hormones, recombinant products and the like. Exemplary therapeutic agents are antibiotics, thrombolytic enzymes such as urokinase or streptokinase, insulin, growth hormone, chemotherapeutics such as adriamycin and antiviral agents such as interferon and acyclovir.

Further information such as treatment regimens, structures, toxicity and the like about the therapeutic agents can be found in the *The Pharmaceutical Basis of Therapeutics*, Goodman et al, eds., 7th ed, The Macmillan Co., New York, N.Y., (1985), and in Goth, A. *Medical Pharmacology*, 9th ed., the C. V. Mosby Co., St. Louis, Mo., (1978) and in the citations therein.

The pharmaceutical compositions of this invention contain swellable latex microgel particles of a copolymer of the present invention and a therapeutic agent associated with these particles. In a preferred embodiment, these pharmaceutical compositions also contain a physiologically tolerable carrier or diluent.

The present invention is also directed to methods of treatment. In these methods a therapeutically effective amount of a pharmaceutical composition containing particles of this invention and a therapeutic agent associated therewith is administered to a host mammal, and the therapeutic agent is then released from the administered particles over a prolonged period of time.

The present invention is also directed to diagnostic methods wherein particles of copolymers of the present invention with or without an associated diagnostic agent are utilized. In a preferred embodiment, the copolymer particles associated with or without a diagnostic agent are administered to a host mammal. Particularly useful diagnostic methods include MRI/NMR, CT (computed tomography), X-ray, radiodiagnosic and ultrasound.

The term "diagnostic agent" as used herein refers to a compound which acts as a contrast agent and thereby produces a detectable indicating signal in the host mammal. The detectable indicating signal may be gamma-emitting, radioactive, echogenic, fluoroscopic or physiological and the like.

The copolymer microparticles of this invention may be prepared by conventional emulsion polymerization procedures, as for example those described in W. R. Sorenson and T. W. Campbell, Preparative Methods of Polymer Chemistry, 2nd Ed. (1968), Wiley, N.Y., N.Y. and M. P. Stevens, Polymer Chemistry, an Introduction, (1975) Addison Wesley Publishing Co. Inc., London, Eng.

Certain specific examples are provided hereinbelow for purposes of illustration only and are not to be taken as limiting.

EXAMPLE 1

Preparation of Poly(methyl methacrylate-co-2-hydroxyethyl methacrylate-co-methacrylic acid-co-ethylene dimethacrylate) microparticles (Weight ratio 57/30/10/3)

A composition was prepared from 1000 ml of an aqueous solution containing 1.2 g of sodium dodecylsulfate and 30 g of a monomer mixture of 57% by weight methyl methacrylate, 30% by weight 2-hydroxyethyl methacrylate, 10% by weight methacrylic acid, and 3% by weight ethylene dimethacrylate. The mixture was degassed with argon and 0.13 g of ammonium persulfate was added. The mixture was polymerized while stirring at 85° C. for 3 hours. The resulting fine dispersion of copolymer nanoparticles was filtered to remove any coarse agglomerates that may have formed and the pH was adjusted to 7 using 0.1N potassium hydroxide. The dispersion was stirred with 10 g of a mixed bed of ion-exchange resin (Amberlite MB-1 sold by Rohm & Haas) for 1 hour, filtered and then diafiltered against water using a 1000 molecular weight cut off polysulfone membrane until all the surfactant was removed. The average hydrodynamic diameter of the copolymer particles in phosphate buffered saline (PBS, pH=7.4, ionic strength=0.15M) at 25° C. was 0.06 $\mu$m. The hydrodynamic diameters (i.e., swollen in situ) were measured in PBS, by photon correlation spectroscopy, using a Brookhaven Light Scattering Instrument BI-2030 equipped with a He-Ne laser (6342.8 nm). Except where otherwise noted, these conditions were used for all particle size measurements at 25° C. or 37° C. as specified.

EXAMPLE 2

Preparation of Poly[methyl methacrylate-co-poly(ethylene oxide) monomethacrylate-co-methacrylic acid-co-ethylene dimethacrylate] microparticles (Weight ratio 57/30/10/3)

The polymer was prepared by the procedure of Example 1 except that poly(ethylene oxide) monomethacrylate was used in place of 2hydroxyethyl methacrylate. The poly(ethylene oxide) group on the monomer had an average of about 10 recurring units derived from ethylene glycol. The particle size at 37° C. in PBS was about 0.06 μm.

EXAMPLE 3-6

Preparation of a Series of Poly(methyl methacrylate-co-2-hydroxyethyl methacrylate-co-methacrylic acid-co-ethylene dimethacrylate) microparticles (Weight ratio 57/30/10/3)

A series of polymers were prepared by the procedure described in Example 1 except varying the parameters as indicated in Table 1 to obtain the indicated particle sizes.

TABLE I

| Example/Reference | Hydrodynamic Diameter μm | Water g | Monomer g | Surfactant g | Initiator g |
|---|---|---|---|---|---|
| 3 | 0.060 | 1000 | 30 | 1.20 | 0.13 |
| 4 | 0.125 | 1000 | 110 | 1.08 | 0.11 |
| 5 | 0.250 | 1000 | 467 | 1.33 | 0.133 |
| 6 | 0.300 | 1000 | 475 | 1.33 | 0.133 |

The particle sizes were measured in PBS at 25° C.

EXAMPLES 7-10

Preparation of a Series of Poly[methyl methacrylate-co-poly(ethylene oxide) monomethacrylate-co-methacrylic acid-co-ethylene dimethacrylate] microparticles (Weight ratio 57/30/10/3)

A series of polymers were prepared as described in Example 2, except that the variations shown in Table II to obtain the indicated particle sizes. The poly(ethylene oxide) group on the monomer had an average of about 10 recurring units derived from ethylene glycol. The particle sizes were measured in PBS at 37° C.

TABLE II

| Example/Reference | Hydrodynamic Diameter μm | Water g | Monomer g | Surfactant g | Initiator g |
|---|---|---|---|---|---|
| 7 | 0.060 | 1000 | 30 | 1.2 | 0.13 |
| 8 | 0.120 | 1000 | 110 | 1.08 | 0.11 |
| 9 | 0.175 | 1000 | 200 | 1.0 | 0.10 |
| 9a | 0.200 | 1000 | 333.3 | 1.33 | 0.133 |
| 10 | 0.420 | 1000 | 538.5 | 1.54 | 0.154 |

The particle sizes were measured in PBS at 37° C.

EXAMPLES 11 and 12

Appendage of Poly(ethylene oxide) to the Polymer Particles of Example 1 Having an Average Diameter of about 0.06 μm (swollen in PBS)

The grafting of polyethylene oxide [monodisperse poly(ethylene oxide) from Polysciences, MW 200 (PEG 200) and MW 600 (PEG 600)] at the surface carboxylate sites were carried out in pH=7.0 NaHCO3 aqueous buffer solution using 1-(3-dimethylaminopropyl)-3-ethylcarbodiimide hydrochloride (obtained from Aldrich Chemical Company, Inc.) (DEC-HCl) as the coupling agent. The extent of grafting, analyzed by potentiometric titration of the unreacted carboxylate, was approximately 50% of the total surface carboxylate groups.

For the small particles (≦0.06 μm in diameter), almost all of the methacrylic acid is on the surface as revealed by potentiometric titration in aqueous solution. First, the following solutions were prepared:

1. A 25 mL aqueous stock solution of the particles (3.7% solids) containing 1.118 mmole methacrylic acid was treated with 0.1N NaHCO3 to maintain the pH at 7.4.

2. An equivalent amount of PETG [1.118 mmole, i.e., of PEG 200 223.6 mg (Example 11) or of PEG 600 670.8 mg (Example 12)] was dissolved in 10 mL water and maintained at pH=7.4 by adding 0.1N NaHCO3.

3. An equivalent amount of the coupling agent DEC-HCl (1.118 mmole or 214.3 mg) was dissolved in 2 mL water.

Solution 3 was added to 1, and then this mixture was added to 2 dropwise with constant stirring while maintaining the pH at 7.0 for 24 hours. The final solution was subjected to exhaustive dialysis for three days to remove any residual PEG or surfactant.

The extent of grafting was calculated by potentiometric titrations of the carboxylate group and found to be approximately 50% of the total carboxylate ions in the particles. The sizes of the particles before and after grafting measured in PBS by photon correlation spectroscopy are shown below:

(original): Example 1: 0.06 μm
(PEG 200 grafted): Example 11: 0.07 μm
(PEG 600 grafted): Example 12: 0.05 μm

EXAMPLES 13 and 14

Appendage of Poly(ethylene oxide) to Polymer Particles of Example 5

1. A 15 mL aqueous stock solution of the particles (13.6% solids) containing 2.35 mmole methacrylic acid was maintained at pH =7.2 by adding 0.42 mL of 0.1N NaHCO3.

2. Poly(ethylene glycol) (0.235 mmole of PEG 200 47 mg (Example 13), or PEG 600 141 mg (Example 14) was dissolved in 2 mL water and adjusted to pH=7.4 with 0.1N NaHCO3.

3. The coupling agent (approximately three times the equivalent of the surface methacrylic acid content, i.e., 140 mg or 0.73 mmole DEC-HCl) was dissolved in 2 mL water and adjusted to pH=7.4 with NaHCO3.

The procedures for the reaction and dialysis are the same as described for Examples 11 and 12. The extent of grafting was estimated to be approximately 50%, and the particle sizes as measured in PBS are as follows:

(original): Example 5: 0.25 μm
(PEG 200 grafted): Example 13: 0.262 μm
(PEG 600 grafted): Example 14: 0.25 μm

PROTEIN ADSORPTION

Protein adsorption measurements were made by two separate procedures (1) Hydrodynamic size measurements by photon correlation spectroscopy, and (2) The Sedimentation Method. The conventional sedimentation technique is not suitable for measurement of small particles of the invention with sizes comparable to those of the proteins, i.e., less than about 0.1 μm; however, the method was used to measure adsorption on large (>0.2 μm) particles.

The hydrodynamic size measurements were made in situ using photon correlation spectroscopy techniques similar to those described by J. Lee, P. A. Martic, and J. S. Tan, J. Colloid Interface Sci. (in press), B. W. Morrissey and C. C. Han, J Colloid and Interface Sci., 65, 423 (1978), and B. D. Fair and A. M. Jamieson, ibid. 77, 525 (1980). They were performed on 5 mL dispersions of the particles in phosphate buffered saline (PBS) containing from 0.013 to 2.5 mg of polymer solids in the absence and in presence of specific proteins added over a wide range of concentrations up to 5 mg/mL. The measurements were made at 25° C. and/or at 37° C. using a Brookhaven Light Scattering Instrument BI-2030 equipped with an He-Ne laser (623.5 nm) with a deviation in diameter of ±2%. The specific proteins employed were human serum albumin (HSA), fibrinogen (FIB), and whole blood plasma protein. The polymer/protein compositions in the figures are expressed as weight fraction of polymer which is plotted (see the accompanying figures) with pure polymer solution=1.0 on the left and pure protein solution=0.0 on the right, versus particle diameter in Angstroms.

EXAMPLE 15

Figure 1:
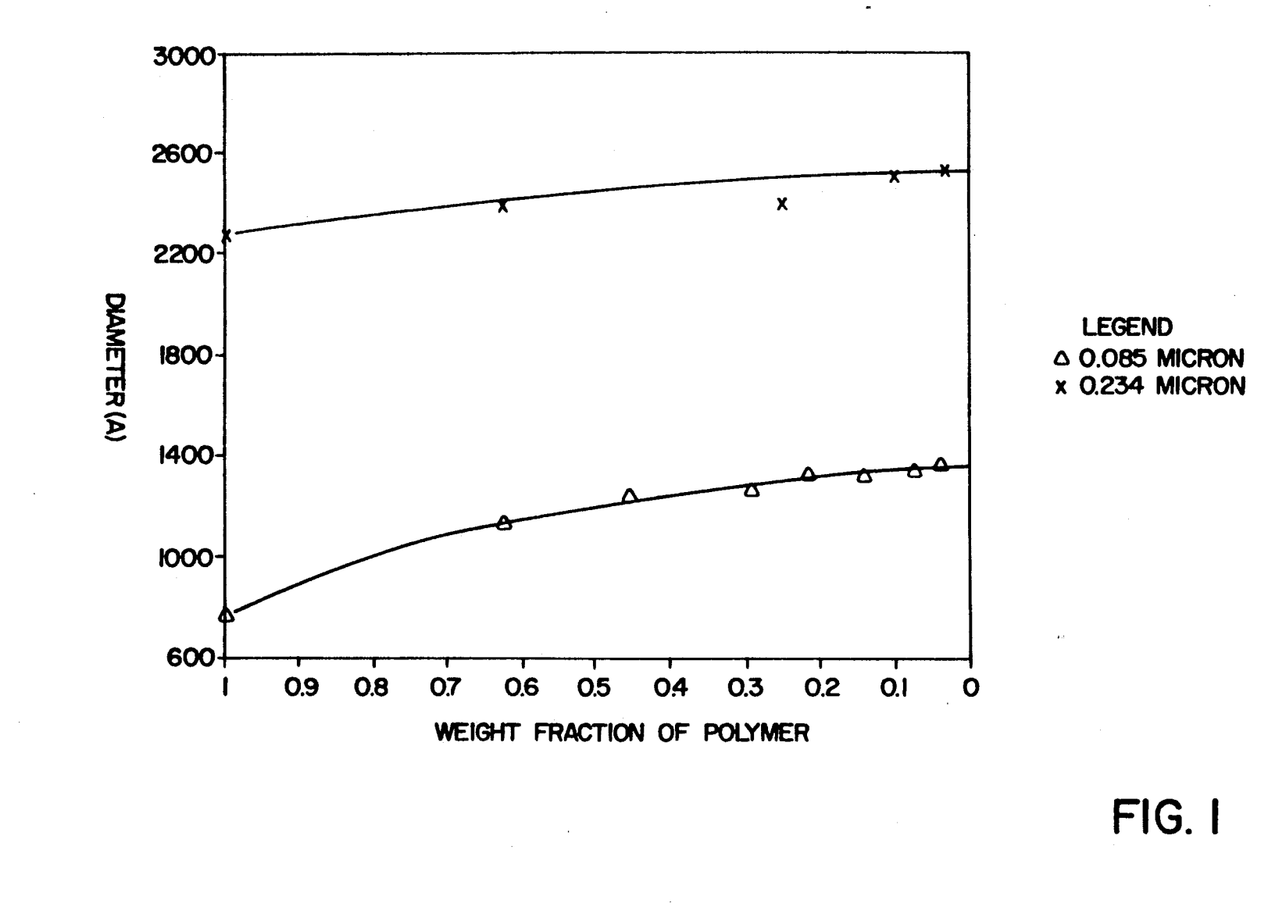
FIGS. 1 and 2 are graphs that plot human serum albumin adsorption in phosphate buffered saline for polystyrene control particles and polymer particles of the present invention, respectively.

Control experiments were performed at 25° C. with polystyrene beads purchased from Seradyn having diameters of 0.085 μm and 0.234 μm. The beads were added as described above at 25° C. with human serum albumin in phosphate buffered saline (PBS) and the measurements made and plotted (FIG. 1) to show that the polystyrene beads of both initial sizes continued to increase in size as the HSA concentration was increased indicative of albumin adsorption. The polystyrene beads thus did not prevent adsorption of the protein.

EXAMPLE 16

Adsorption of Human Serum Albumin

Figure 2:
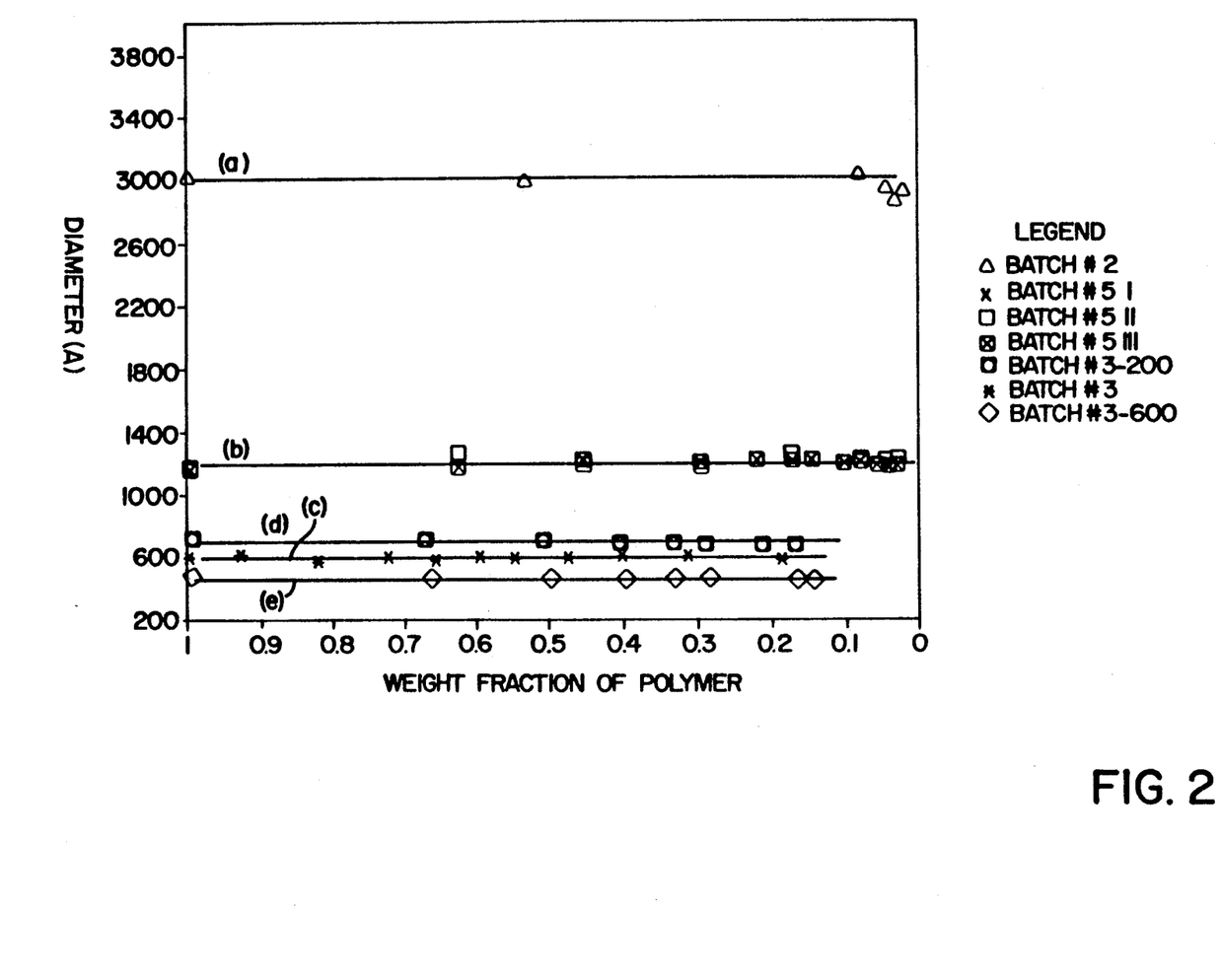

Another series of experiments was performed as in Example 15 except using the following polymers:

| Batch in FIG. 2 | Polymer (Example No.) | Approximate Initial Particle Size (μm) | Appended Poly(ethylene oxide) (PEG) |
|---|---|---|---|
| 2 | 6 | 0.30 | No |
| 5 I | 4 | 0.125 | No |
| 5 II | 4 | 0.125 | No |
| 5 III | 4 | 0.125 | No |
| 3-200 | 11 | 0.07 | Yes |
| 3 | 1 | 0.06 | No |
| 3-600 | 12 | 0.05 | Yes |

The data (plotted in FIG. 2) shows that the particle sizes of all the polymers remain constant as the weight fraction of polymer goes from 1.0 to 0, while the weight fraction of HSA goes from 0 to 1.0, indicating that all the polymers, with and without grafted PEG, show little tendency toward HSA adsorption at the particle sizes tested.

A separate experiment, however, using the particles of Example 4 (FIG. 2, batch 5) in water at pH=5.5, plotted the same way, showed that at the lower pH, some HSA was adsorbed. This is attributed to the slightly positive charge on HSA and the incomplete ionization and swelling of the particles in water. Thus, it is important that the pH be above about 7 for reduced HSA adsorption by these beads.

EXAMPLE 17

Adsorption of Human Fibrinogen

Figure 3:
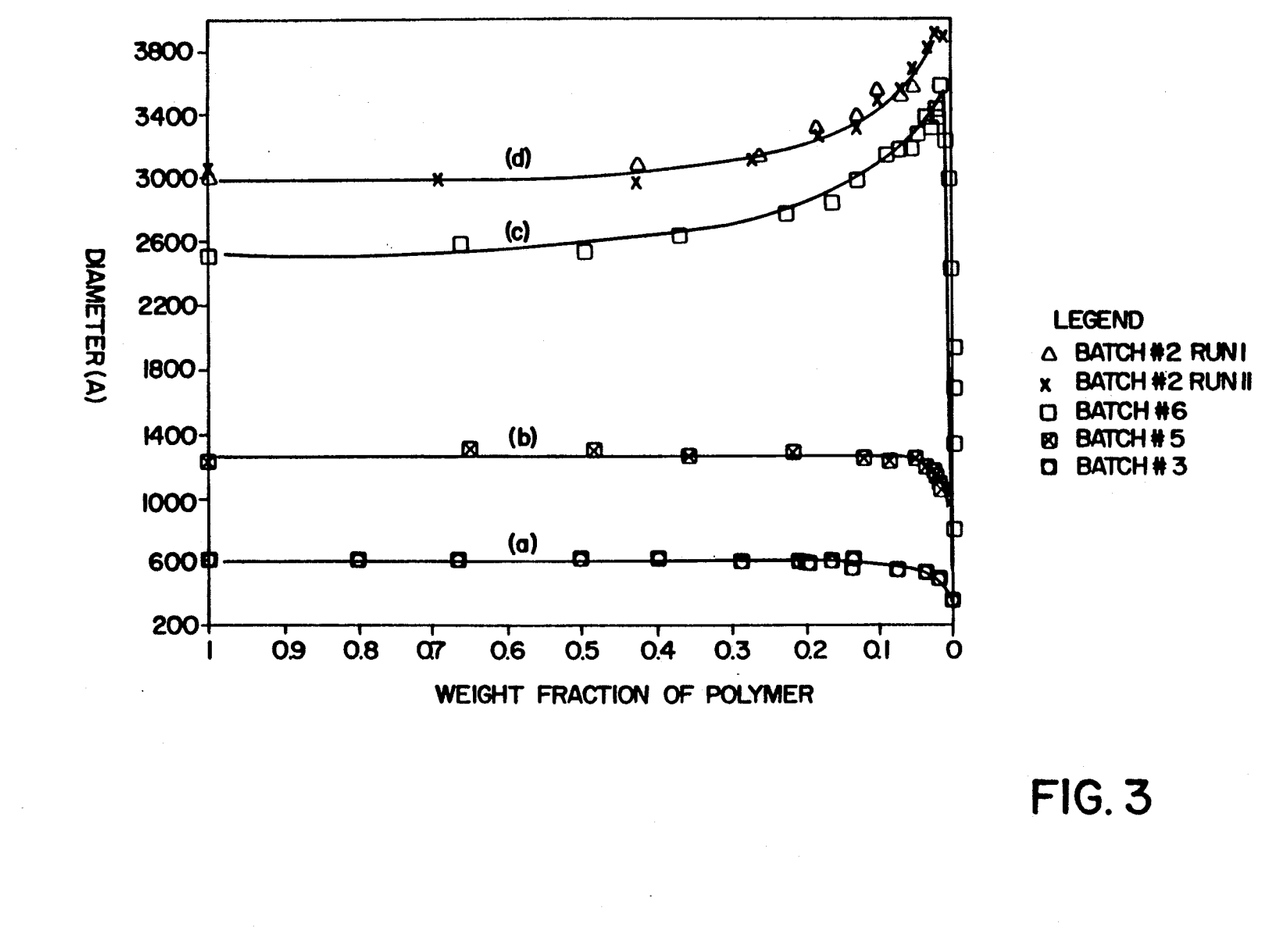
FIGS. 3, 4 and 5 are graphs that plot human fibrinogen adsorption in phosphate buffered saline for polymer particles of the present invention.
Figure 5:
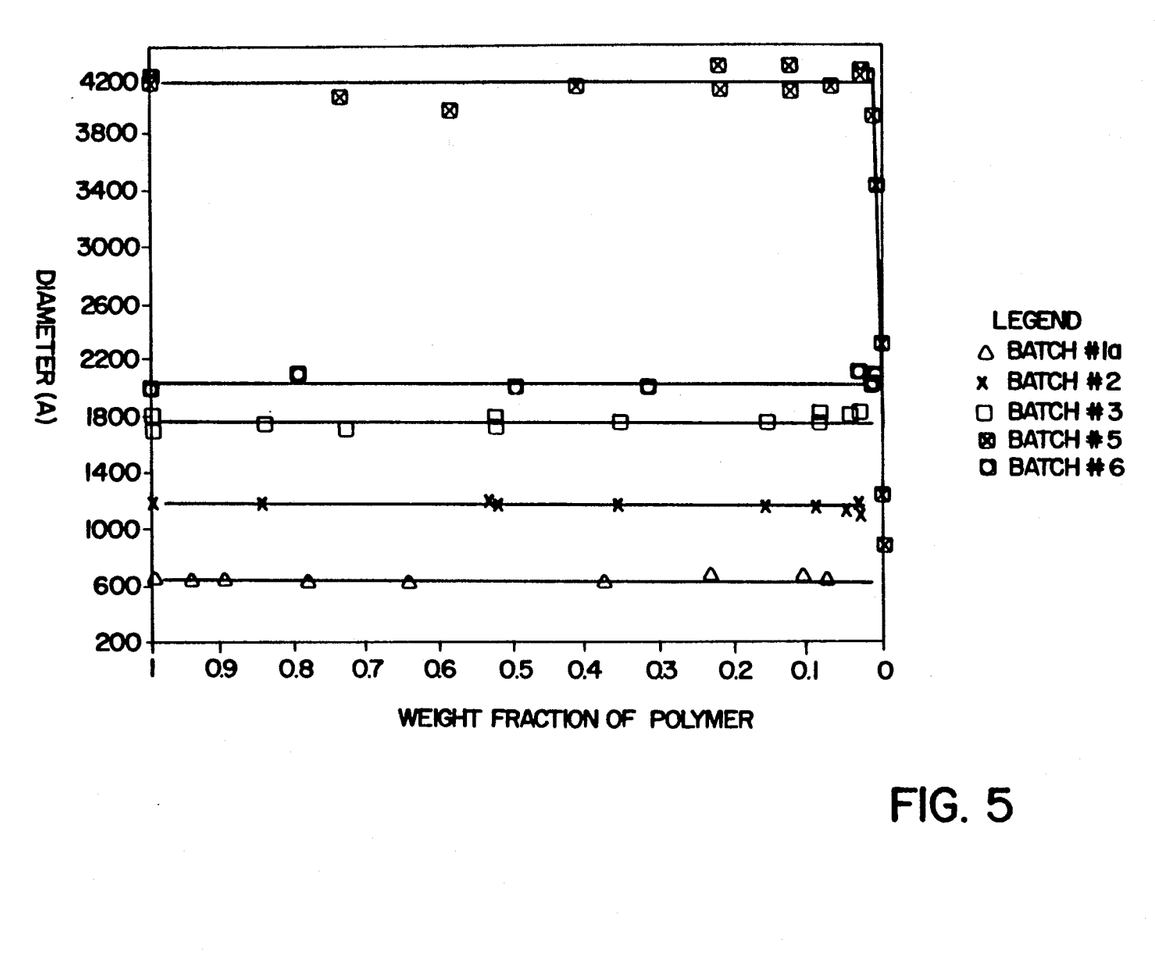

Another series of experiments was performed as in Example 16, again at 25° C. in PBS, except using fibrinogen in place of HSA in concentrations ranging up to 3 mg/mL instead of 5 mg/mL and the following polymers:

| Batch in FIG. (3 or 5) | Polymer (Example No.) | Approximate Initial Particle Size (μm) | Appended (PEG) |
|---|---|---|---|
| 2 (3) | 6 | 0.30 | No |
| 6 (3 and 5) | 5 | 0.25 | No |
| 5 (3) | 4 | 0.125 | No |
| 3 (3) | 1 | 0.06 | No |
| 6-200 (5) | 13 | 0.258 | Yes |

Figure 4:
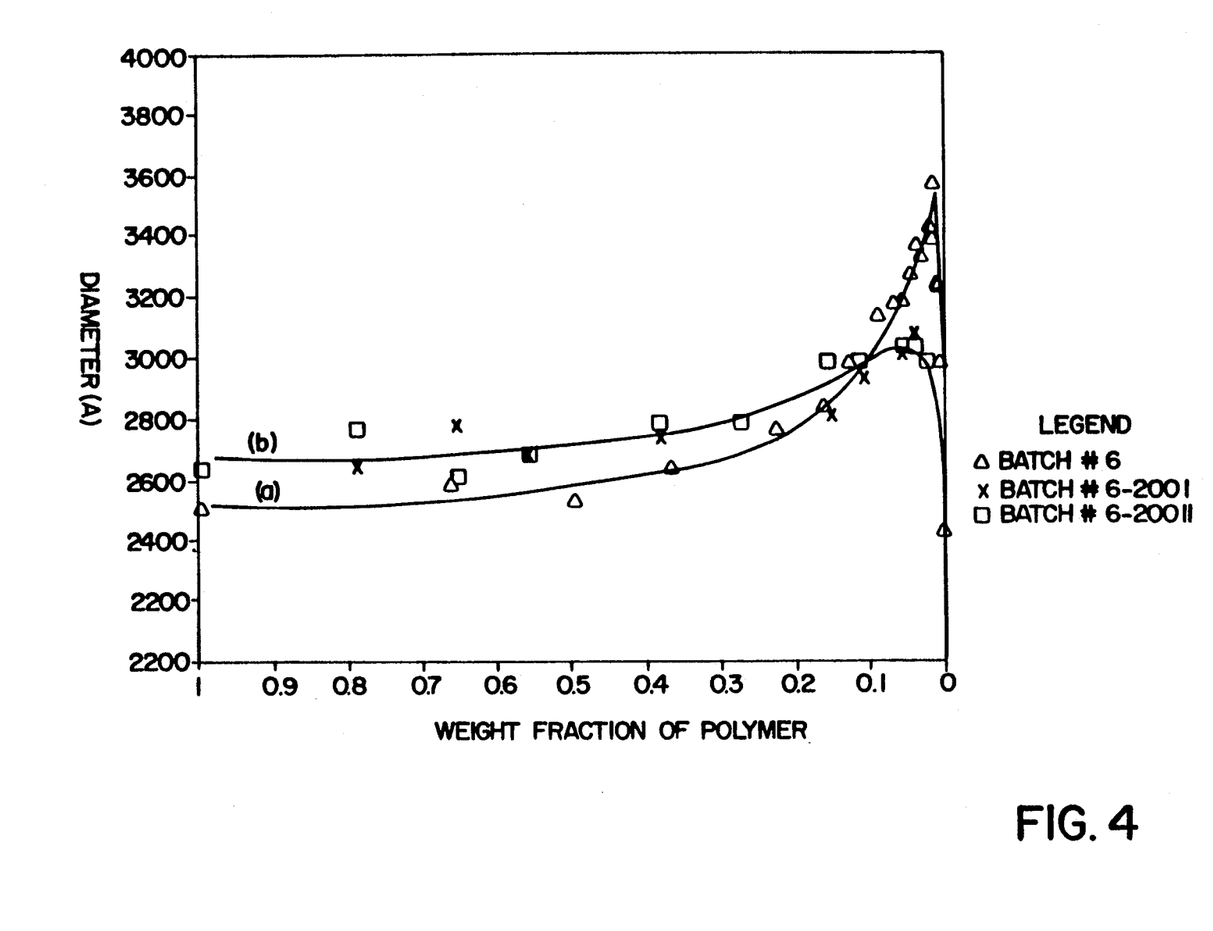

The 0.06 μm and 0.125 μm beads remain of constant size in the presence of fibrinogen up to polymer weight fraction 0.05, showing very strong resistance to fibrinogen adsorption; however, the larger particles without PEG appended increase in size with increasing fibrinogen concentration (FIG. 3). This is believed to be the result of the greater available surface area per particle on the larger particles to accommodate adsorption of fibrinogen. On the other hand, when PEG is appended to the larger particles, they show less affinity to adsorb fibrinogen than do the same particles without appended PEG (FIG. 4).

The measured average particle sizes are reduced (FIG. 3-5) when the fibrinogen concentration is high as a result of scattering due to the excess, small-sized fibrinogen (~0.035 μm). The bimodal size distribution as observed in the scattering data is an indication of excess nonreacting fibrinogen molecules coexisting with the inert small particles or with the polymer/fibrinogen adsorption complex of the larger particles.

The fibrinogen adsorption is much less than the PEG is appended during the preparation process by copolymerization with a monomer containing the PEG as in Examples 2 and 7 to 10 rather than by grafting the PEG onto a preformed polymer as in Examples 11 to 14 since the former method more efficiently incorporates the PEG side chains. Another series of experiments as above except at 37° C. and using PEG containing polymers prepared as described in Examples 2 and 7 to 10 was performed using the following polymers:

| Batch in FIG. 5 | Polymer (Example No.) | Approximate Initial Particle Size (μm) | Appended (PEG) |
|---|---|---|---|
| 1a | 7 | 0.06 | Yes |
| 2 | 8 | 0.12 | Yes |
| 3 | 9 | 0.175 | Yes |
| 5 | 10 | 0.42 | Yes |
| 6 | 9a | 0.20 | Yes |

The plotted date (FIG. 5) shows that all these polymers are resistant to fibrinogen adsorption, indicating that even the larger particles show protein resistance when a sufficient amount of the PEG side chain is incorporated.

This example illustrates that large particles without PEG appended do not adequately prevent fibrinogen adsorption, whereas small particles with or without PEG side chains and large particles with sufficient PEG side chains do strongly inhibit fibrinogen adsorption. It should be mentioned in this example that of the three types of protein investigated, fibrinogen has the strongest tendency to adsorb to polymer particles, whole plasma next, and HSA the least.

EXAMPLE 18

Adsorption of Human Whole Blood Plasma Protein

Figure 6:
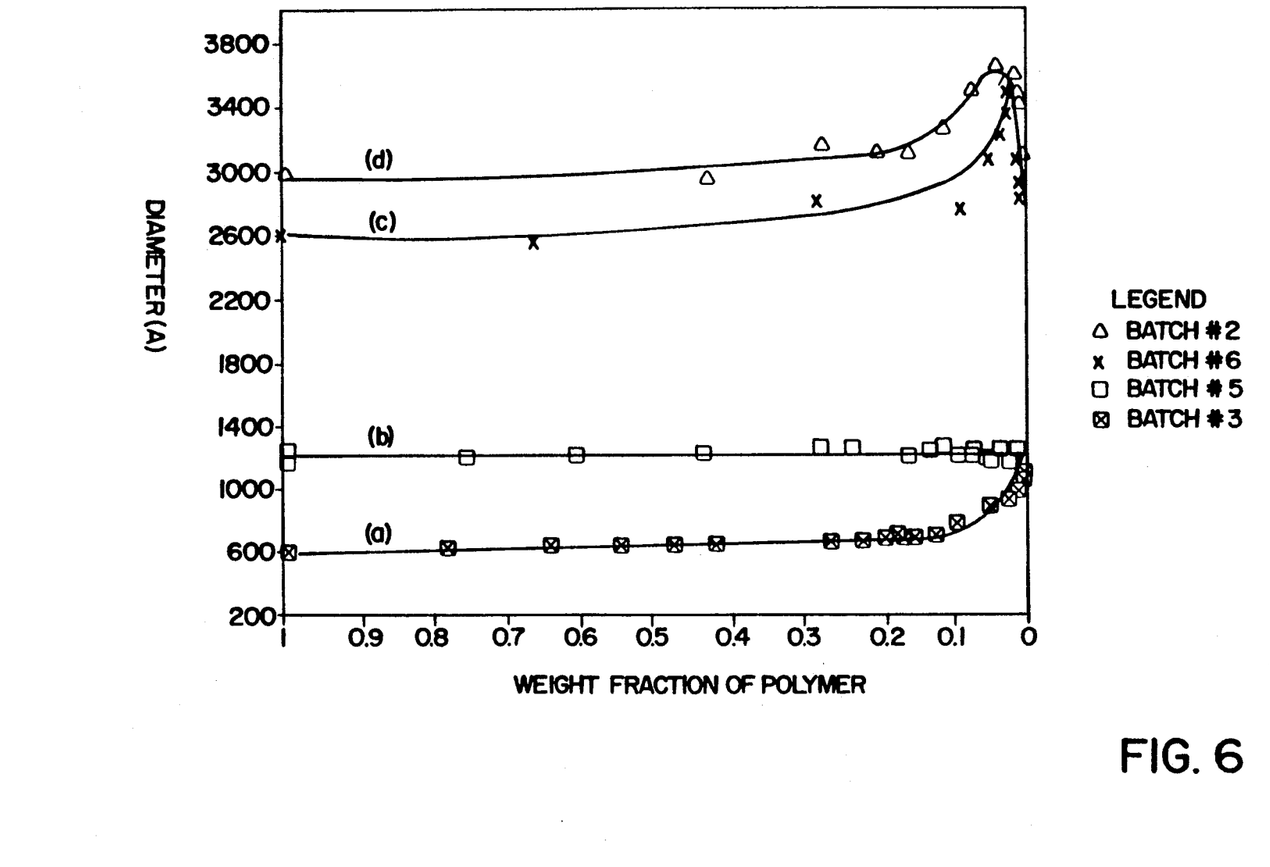
FIGS. 6 and 7 are graphs that plot whole plasma protein adsorption in phosphate buffered saline for polymer particles of this invention.
Figure 7:
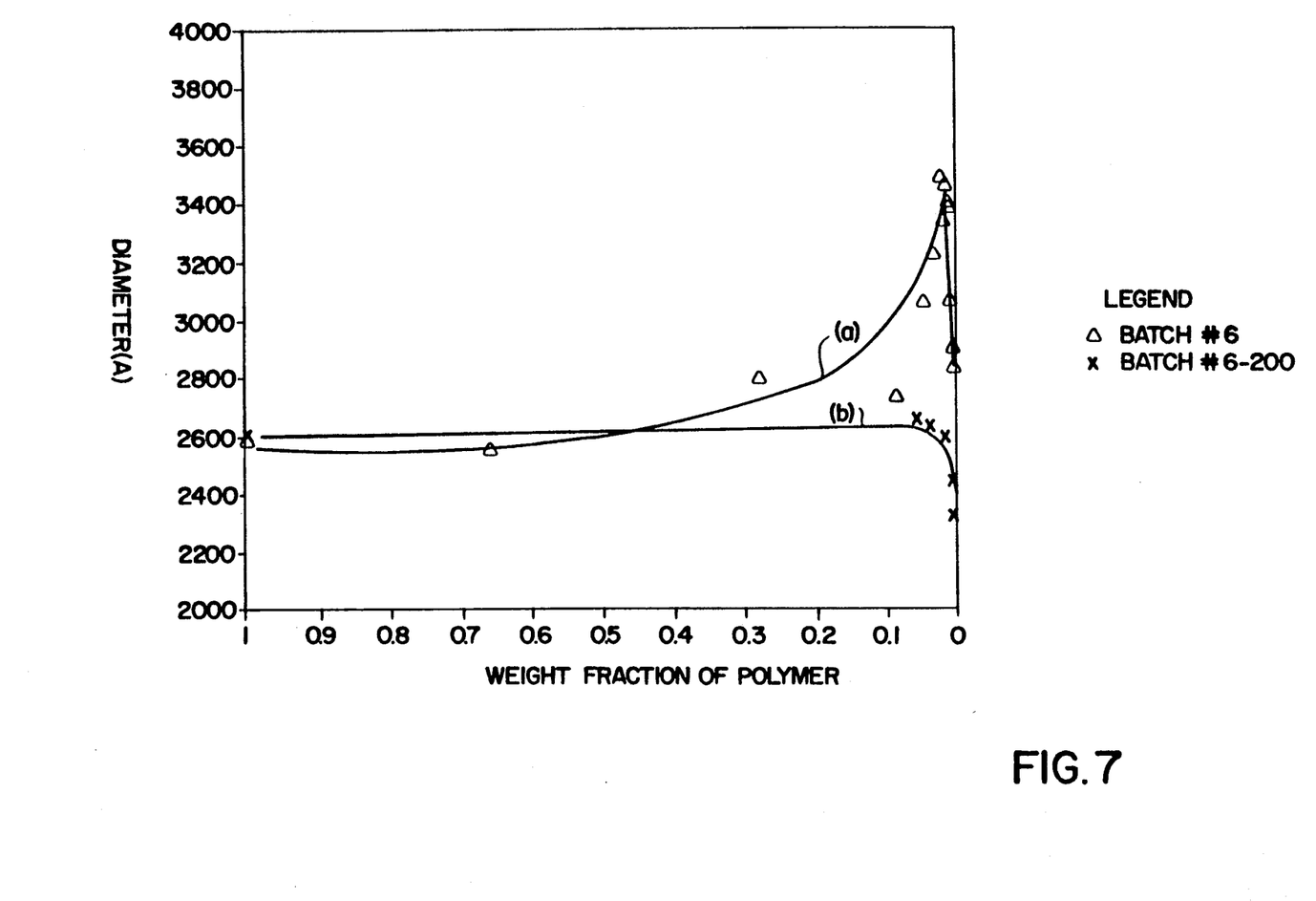

A series of experiments were performed as in Example 16 except using the following polymers:

| Batch in FIG. (6 or 7) | Polymer (Example No.) | Approximate Initial Particle Size (μm) | Appended (PEG) |
|---|---|---|---|
| 2 (6) | 6 | 0.30 | No |
| 6 (6 and 7) | 5 | 0.25 | No |
| 5 (6) | 4 | 0.125 | No |
| 3 (6) | 1 | 0.06 | No |
| 6–200 (7) | 13 | 0.257 | Yes |

The plotted date (FIG. 6) shows that the small (i.e., 0.6 and 0.125 μm) particles also show little tendency toward plasma protein adsorption whereas the larger (0.25 and 0.30) size particles without any PEG side chains do adsorb some of the protein. Note that the apparent increase in size of the 0.06 μm particles at high protein plasma concentration is caused by the presence of excess plasma proteins in the solution which have an average size of about 0.115 μm rather than by protein adsorption to the polymer particles. This is supported by size distribution data from light scattering in this region as well as by the absence of size increase when a small amount of the polymer particles is added to a pure plasma protein solution.

The plotted data (FIG. 7) for Examples 6 and 13 show the dramatic reduction in protein plasma adsorption when the larger size particles have PEG grafted onto them. The negligible size increase of the grafted particle (of Example 13) indicates that, while size is critical, surface modification offers an added dimension for solving protein adsorption problems. This is illustrated further in the next example.

EXAMPLE 19

Study of Protein (Fibrinogen) Adsorption to Larger Size Particles by the Sedimentation Technique Another method for evaluating the extent of protein adsorption is the Sedimentation Technique. This method directly measures the amount of protein adsorbed to the surface of the particle (mg/m$^2$), in contrast to the diameter measurements described earlier which merely measure the increase ion hydrodynamic diameter as a result of adsorption. The hydrodynamic diameter measurements can be used for all size particles; however, the sedimentation method is only applicable to larger particles (>0.2 μm). Polymer particles having no appended PEG prepared as described in Example 5 (about 0.26 μm measured by photon correlation spectroscopy) and particles having PEG side chains prepared as described in Example 9a (about 0.20 μm measured by photon correlation spectroscopy) were studied to observe the adsorption thereto by fibrinogen in PBS at 25° C.

The aqueous solutions containing a constant amount of particles (13.6 mg or 10 mg) and various amounts of fibrinogen with a total volume of 1.0 to 1.5 mL in PBS were kept in 1.7 mL-plastic vials at room temperature with gentle rocking overnight. These samples were then centrifuged at 14,000 rpm in an Eppendorf Centrifuge for 1 hour, and the supernatant liquids were analyzed by U.V. spectrophotometry for the unbound protein concentration. For each mixture, an accompanying blank solution containing the same amount of protein without particles was prepared under the same conditions.

Shown in Table III is the data for two series of runs for particles of Example 5. The concentrations (mg/mL) of the total fibrinogen and the free fibrinogen are listed under the first and second columns, respectively. The amount of bound fibrinogen (mg) and the corresponding bound fibrinogen per unit area of the particle surface (mg/m$^2$) are listed under the third and the fourth columns, respectively. Also included in the parentheses are the experimental uncertainties estimated for the low and high fibrinogen concentration regions.

Table III shows that the extent of adsorption for the 0.26 μm size particles is substantial at the high fibrinogen concentration region, i.e., ~3 mg/mL; however, it is significantly less than the value of ~15 mg/mL that we obtained for polystyrene/fibrinogen. Thus, adsorption behavior is consistent with the particle size increase of the same particle owing to fibrinogen adsorption as described previously (curve c, FIG. 3) by photon correlation spectroscopy.

Similar adsorption data for particles of Example 9a are shown in Table IV. Again each mixture was accompanied by a blank run prepared under identical conditions. Based on the range of experimental uncertainties (±0.05 to ±0.25 mg/mL) for the concentration regions studied, we have concluded that fibrinogen adsorption is too little to be measured for the present 0.2 μparticles. This is also consistent with the absence of fibrinogen adsorption, as indicated by the constant size of the same particles upon addition of fibrinogen as shown in FIG. 5.

EXAMPLE 20

Inertness of the Polymer Particles

Figure 8:
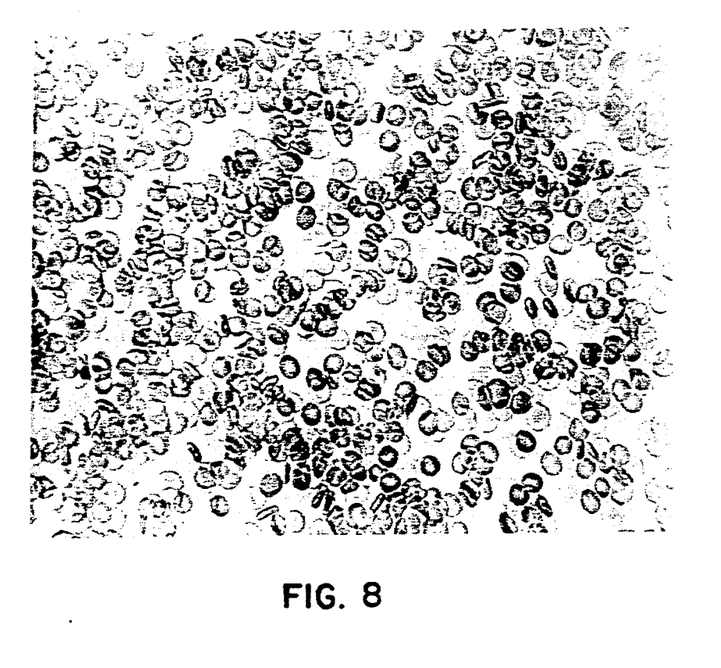
FIG. 8 is a photomicrograph of red blood cells that have been washed in phosphate buffered saline.
Figure 9:
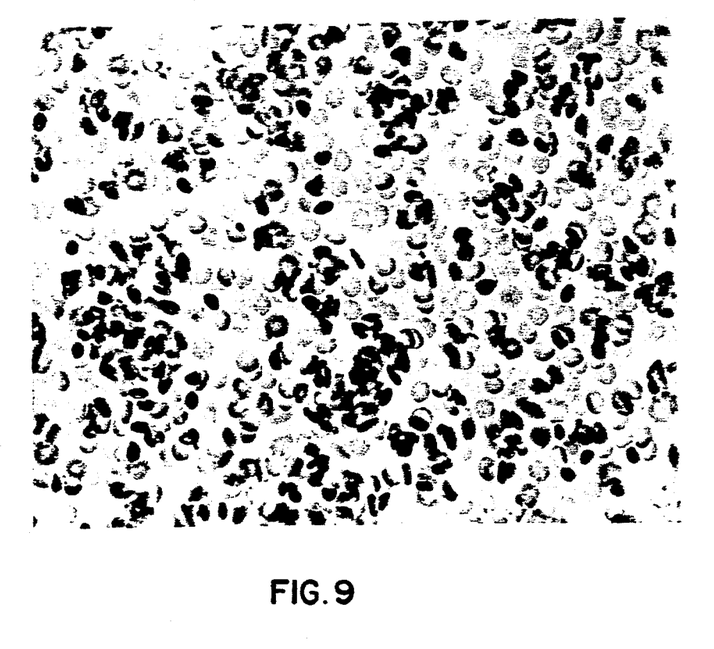
FIG. 9 is a photomicrograph of red blood cells that have been treated with polymer particles of this invention.

To show that the polymer particles did not lyse, aggregate, or otherwise adversely affect the cells, photomicrographs were taken of (1) a sample of human red blood cells that had been washed and suspended in PBS (FIG. 8) and (2) another sample of cells prepared the same way but additionally having been treated with 0.5% of the particles of Example 3 (FIG. (9). The photomicrographs appear to be identical showing no lysis of the blood cells, coagulation, or other visually adverse effects.

TABLE III

Data for the Adsorption of Fibrinogen on Particles of Example 5 (0.26 μm in diameter)

Particle surface area = 0.0218 m$^2$/mg

| | [FIB]$_{total}$ (mg/mL) | [FIB]$_{free}$ (mg/mL) | [FIB]$_{bound}$ (mg) | [FIB]$_{bound/unit\ area}$ (mg/m$^2$) |
|---|---|---|---|---|
| Run I | 0.490 | 0.374 | 0.118 | 0.398 (δ = ±0.05 mg/m$^2$)* |
| W$_{polymer}$ = | 0.962 | 0.834 | 0.133 | 0.449 |
| 13.6 mg | 1.415 | 1.276 | 0.147 | 0.496 |

TABLE III-continued

Data for the Adsorption of Fibrinogen on Particles of Example 5
(0.26 μm in diameter)

Particle surface area = 0.0218 m²/mg

| | $[FIB]_{total}$ (mg/mL) | $[FIB]_{free}$ (mg/mL) | $[FIB]_{bound}$ (mg) | $[FIB]_{bound/unit\ area}$ (mg/m²) |
|---|---|---|---|---|
| | 2.273 | 1.928 | 0.345 | 1.164 |
| | 3.261 | 2.744 | 0.594 | 2.004 |
| | 4.167 | 3.531 | 0.763 | 2.575 |
| | 5.000 | 4.271 | 0.911 | 3.074 (δ = ±0.25 mg/m²) |
| Run II | 0.459 | 0.429 | 0.047 | 0.192 (δ = ±0.05 mg/m²) |
| $W_{polymer}$ = | 1.116 | 1.033 | 0.146 | 0.670 |
| 10 mg | 2.130 | 2.003 | 0.182 | 0.836 |
| | 3.904 | 3.752 | 0.318 | 1.459 |
| | 5.406 | 5.318 | 0.517 | 2.371 |
| | 6.693 | 6.666 | 0.695 | 3.191 (δ = ±0.25 mg/m²) |

*δ = experimental uncertainty

TABLE IV

Data for the Adsorption of Fibrinogen on Particles of Example 9a
(0.2 μm in diameter)

(Particle surface area ~0.027 m²/mg)

| | $[FIB]_{total}$ (mg/mL) | $[FIB]_{free}$ (mg/mL) | $[FIB]_{bound}$ (mg) | $[FIB]_{bound/unit\ area}$ (mg/m²) |
|---|---|---|---|---|
| Run I | 0.459 | 0.454 | 0.005 | 0.019 (δ = ±0.05 mg/m²)* |
| $W_{polymer}$ = | 1.116 | 1.119 | −0.003 | −0.011 |
| 10 mg | 2.129 | 2.124 | 0.006 | 0.022 |
| | 3.904 | 3.912 | −0.010 | −0.037 |
| | 5.406 | 5.413 | −0.010 | −0.037 |
| | 6.693 | 6.661 | 0.045 | 0.167 (δ = ±0.25 mg/m²) |

*δ = experimental uncertainty

The foregoing specification, including the specific embodiments and Examples, is intended to be illustrative of the present invention and is not to be taken as limiting. Numerous other variations and modifications can be made without departing from the true spirit and scope of the present invention.

We claim:

1. A copolymer microgel derived from:
   a) from about 5 to about 30 weight percent of recurring units derived from free carboxylic acid group containing vinyl monomers;
   b) from about 1 to about 25 percent of recurring units derived from monomers that have poly(alkylene oxide) groups appended thereto;
   c) from about 20 to about 90 weight percent of recurring units derived from oleophilic monomers which contain alpha, beta-ethylenically unsaturated hydrocarbon groups; and
   d) from about 5 to about 40 weight percent of recurring units derived from nonionic hydrophilic group-containing monomers containing poly(alkylene oxide) or polar groups.

2. The copolymer microgel according to claim 1 wherein said copolymer microgel is derived from alkyl methacrylates.

3. The copolymer microgel according to claim 1 wherein said polyalkylene oxide groups are polyethylene oxides.

4. The copolymer microgel according to claim 1 wherein said copolymer microgel comprises recurring units derived from methyl methacrylate, poly(ethylene oxide) methacrylate, methacrylic acid and ethylene dimethacrylate.

5. The copolymer microgel according to claim 1, further comprising 0.5 to about 25 weight percent of recurring units derived from cross-linking monomers having two or more addition-polymerizable vinyl groups, that produce a swellable three-dimensional polymer network upon polymerization.

6. The copolymer microgel according to claim 1 wherein said copolymer microgel is a substantially protein non-absorbent particle.

7. The non-adsorbent particle according to claim 6 wherein said non-adsorbent particle is a microparticle having a median water swollen diameter of about 0.01 to about 1.0 micrometers.

* * * * *